United States Patent [19]

Riehl

[11] 4,210,815
[45] Jul. 1, 1980

[54] X-RAY APPARATUS SERVO SYSTEM

[75] Inventor: Mark E. Riehl, Waukesha, Wis.

[73] Assignee: General Electric Company, Schenectady, N.Y.

[21] Appl. No.: 962,274

[22] Filed: Nov. 20, 1978

[51] Int. Cl.² .................... G01N 21/34; G01N 23/04
[52] U.S. Cl. ............................ 250/445 R; 250/439 R
[58] Field of Search ............. 250/445 R, 445 T, 444, 250/446, 447, 448, 449, 450, 451, 490, 521, 522, 523, 524, 525, 439

[56] References Cited

U.S. PATENT DOCUMENTS

| | | | |
|---|---|---|---|
| 4,024,401 | 5/1977 | Bernstein et al. | 250/445 R |
| 4,024,403 | 5/1977 | Bernstein et al. | 250/445 R |

*Primary Examiner*—Craig E. Church
*Assistant Examiner*—Thomas P. O'Hare
*Attorney, Agent, or Firm*—Ralph G. Hohenfeldt

[57] ABSTRACT

An x-ray receptor is translatable in x and y directions relative to the angulation axis of an x-ray source. Servo motors angulate the source and receptor coordinately with translation so the central ray of the x-ray beam from the source will be perpendicular to the input plane of the receptor when an x-ray exposure is made. New circuitry prohibits making an exposure until the source and receptor are properly angulated. Potentiometers develop signals corresponding with x and y distances and these are divided to get a servo motor command signal corresponding with the tangent of the angulation angle $\theta$. Potentiometers driven coordinately with the receptor and source produce respective sets of signals corresponding with true instantaneous or real time angles $\theta$ and tangent $\theta$. The first tangent $\theta$ command signal is continuously compared with the other tangent $\theta$ signals and the first tangent $\theta$ signal is independently compared with the actual angle $\theta$ with separate window comparators. As long as any pair of signals do not compare, the x-ray tube power supply is disabled.

4 Claims, 5 Drawing Figures

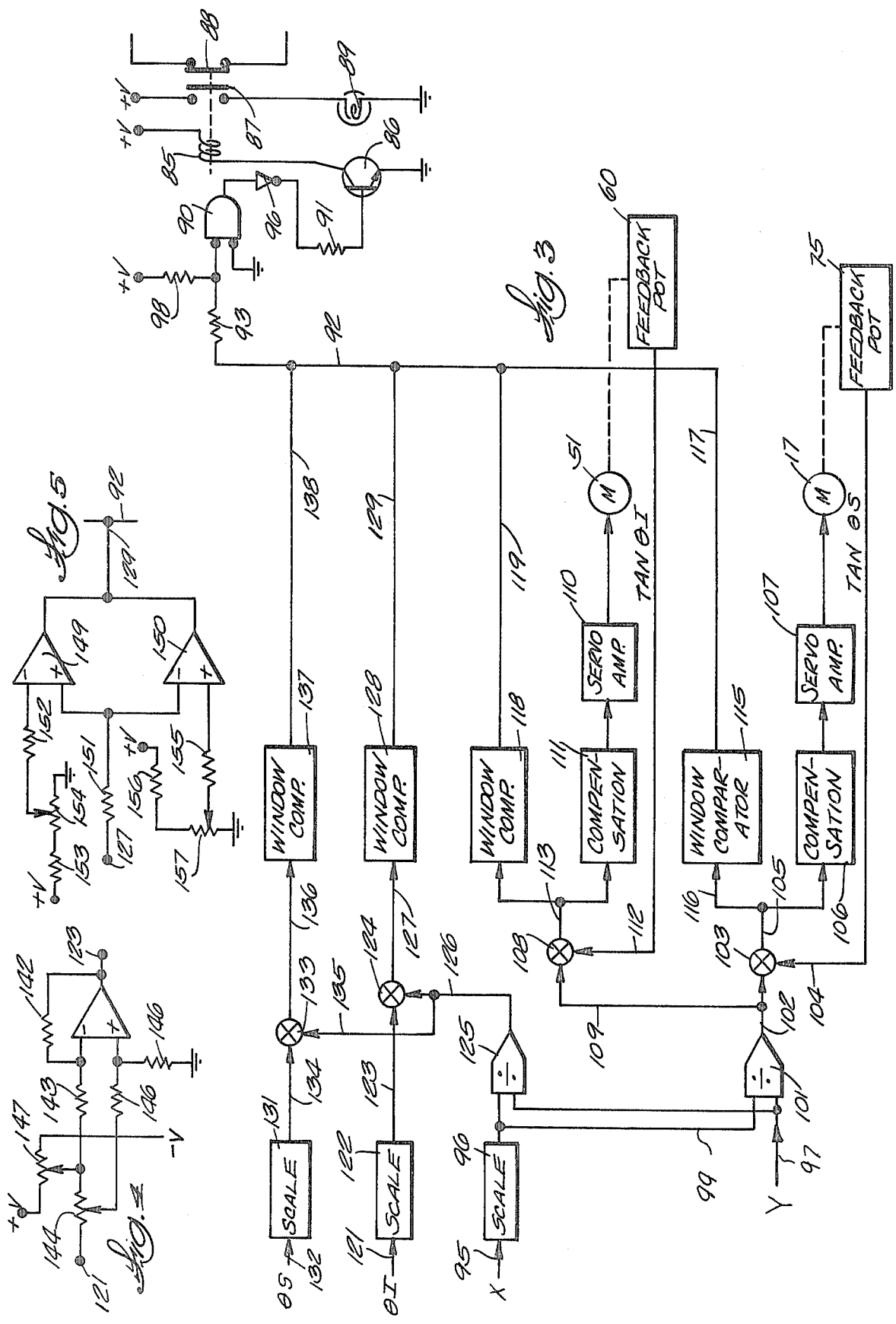

X-RAY APPARATUS SERVO SYSTEM

This invention relates to x-ray apparatus and, in particular, to a servo control system which has improvements for assuring that an x-ray source and an x-ray image receptor are properly angulated and aligned and that the control system is functioning properly before an x-ray exposure can be made.

The new servo system control is applicable to many kinds of diagnostic x-ray apparatus but will be illustrated in connection with cardiovascular examination apparatus. A predecessor cardiovascular apparatus to which the new servo control system is applicable and over which this invention is an improvement, is shown in U.S. Pat. No. 4,024,403 which is owned by the assignee of this invention and is incorporated herein by reference.

Cardiovascular apparatus is a good example of a diagnostic x-ray apparatus where there is a need for being able to angulate an x-ray source and an x-ray image receptor so that an x-ray view of an anatomical plane that lies at an angle with respect to vertical or horizontal can be made with the central ray of the x-ray beam perpendicular to the anatomical plane and to the plane of the x-ray sensitive member in the image receptor. This requires angulating the x-ray image receptor and the x-ray source jointly. As an example, angulation is necessary for viewing the left anterior descending artery on the heart. When the cardiovascular examination subject is lying horizontally on an x-ray table, this artery is disposed in a plane which is at an angle relative to horizontal and vertical. The artery might be shadowed by other anatomy and would appear to be foreshortened in the radiographic or fluoroscopic view if the x-ray source and image receptor were in vertical alignment when the x-ray exposure is made.

In x-ray apparatus such as that which is specially designed for cardiovascular examinations, an x-ray source is mounted on one side of a patient supporting table for being driven angularly with a servo motor and an x-ray image receptor such as an electronic image intensifier is mounted on the other side of the table for being shifted longitudinally and vertically to the position where in which it is angulated correspondingly with a servo motor. The intensifier is angulated synchronously and coordinately with the x-ray source such that the central x-ray beam from the source is perpendicular with the x-ray image input plane of the image receptor at the time an x-ray exposure is to be made. The x-ray source is preferably enclosed within the x-ray table structure under the top of the table. The x-ray image receptor is mounted on a vertically moveable and horizontally translatable support above the table. The rotational axes of the receptor and x-ray source are parallel.

To take an x-ray view at an angle with respect to vertical through the examination subject's body, and perpendicular to some anatomy lying in a plane that is inclined from vertical, the operator will translate the image receptor lengthwise of the x-ray table and at the desired height over the table so the receptor is not vertically over the focal spot in the x-ray source at that time. Upon this event, the servo control system angulates the receptor properly for whatever horizontal and vertical coordinates the rotational axis of the receptor is at while at the same time the servo control system angulates the x-ray source to the same angle so the central ray of the x-ray beam will be perpendicular to the image input plane of the receptor.

Angulation of the receptor and x-ray source to perpendicularity and alignment requires an amount of time that depends upon the amount of angulation required, the inertia of the system and other factors. If the receptor has not become aligned with the x-ray source before the source is energized, stray radiation, which would otherwise be intercepted, could be projected in the room. An x-ray exposure before angulation is complete would also result in blurred and cut off x-ray views and would require retakes in which case the examination subject would get additional x-ray dosage.

SUMMARY OF THE INVENTION

The primary object of the present invention is to provide in x-ray apparatus means for inhibiting production of x-rays whenever components such as an x-ray source and an image receptor are misaligned for any reason such as due to the delay caused by the component driving system or due to failure of any element in the electrical control circuitry.

In accordance with the invention, means are provided for developing first and second signals proportional to the length of the x and y vectors corresponding to the position to which an x-ray image receptor has been translated from a home position. The x and y vectors are the side opposite and the side adjacent to an angle $\theta$ in a triangle whose apex is coincident with the x-ray source focal spot. The signals corresponding with the x and y vectors are divided to obtain a signal corresponding with $\tan \theta$. There is a servo motor control system and a servo motor for driving each of the x-ray tube and image receptor angularly through the angle $\theta$ which varies with receptor displacement in the x and y directions with respect to the focal spot of the x-ray source. A feedback potentiometer is driven while the motors are operating to produce an output signal which corresponds with $\tan \theta$ for the instantaneous angular positions of the source and receptor. The servo command signal corresponding with $\tan \theta$ resulting from the division of the x and y vectors is continuously compared with the tan of $\theta$ signal corresponding with instantaneous angular position. When the two tangent values are still unequal, an error signal is provided to the servo motor controls which keeps the servo motors running. When the proper angles are reached, the error signals for the source and receptor servo motors are nulled and the motors stop.

The servo error signal is fed to a window comparator which remains in one output state while the servo error signal lies outside of predetermined upper and lower limits and changes state when the signal is within the window or within limits. When in the first state, the comparator inhibits production of x-rays and when the error signal is within the window limits, the x-ray source power supply is enabled.

A redundant or additional circuit is provided for further assuring that no x-ray exposure can be made until the angles of the image receptor and x-ray source are equal. The redundant system compares or sums the signal corresponding with the $\tan \theta$, obtained by division of the x and y vectors, with respective signals corresponding with the actual angle $\theta$ at which the source and receptor are disposed at any instant. For small angular differences, the actual numerical value of $\theta$ is very close to the value of the tangent of $\theta$ in radians which is a known characteristic of the tangent function. The signal values corresponding with the actual present value of the angle $\theta$ for the source and receptor are each continuously summed or subtracted during angulation from the signal corresponding with the tangent of $\theta$ obtained by said division. The output signals from the summing devices are provided to individual window comparators which are also operative to inhibit production of x-rays as long as the error signal, that is, the difference between $\theta$ and $\tan \theta$ falls outside of the limits of the window comparator.

An illustrative embodiment of the new control system which permits making an x-ray exposure only if safe conditions are met will now be described in greater detail in reference to the drawings.

DESCRIPTION OF THE DRAWINGS

FIG. 3 is a block diagram of an x-ray apparatus control system which incorporates the exposure inhibiting improvements;

FIG. 4 is a circuit diagram of a typical signal scaling device used in the FIG. 3 system; and FIG. 5 is a circuit diagram of a typical window comparator which is used in the FIG. 3 system.

DESCRIPTION OF A PREFERRED EMBODIMENT

Figure 1:
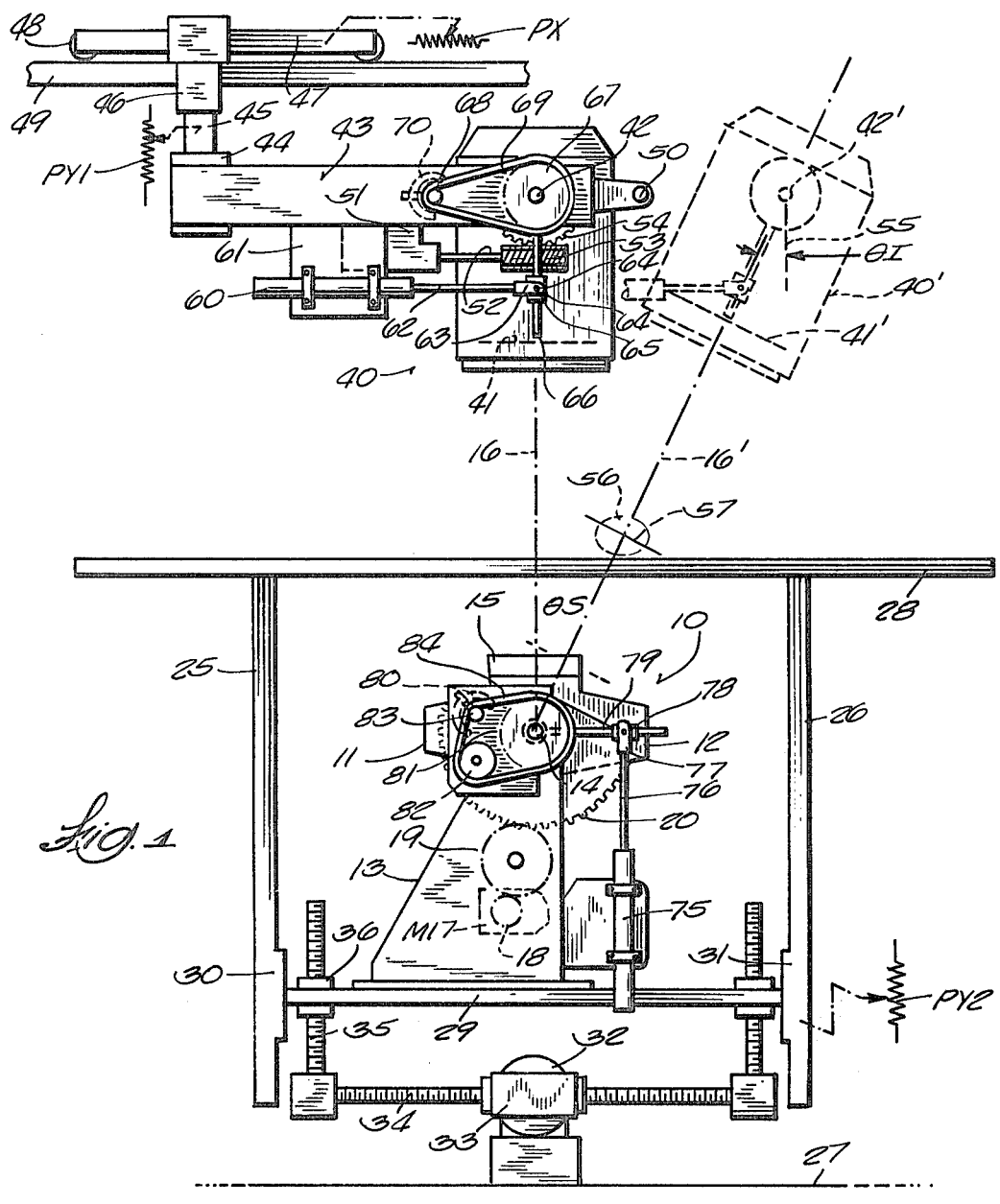
FIG. 1 shows the main components of one type of diagnostic x-ray apparatus in which the new system for preventing making an x-ray exposure until predetermined conditions are met is incorporated.

Referring to FIG. 1, the illustrative x-ray apparatus comprises an x-ray tube casing 10 having opposite ends 11 and 12. The casing is mounted on a stand 13 for angulating on a shaft whose axis 14 is perpendicular to the plane of the drawing. The customary x-ray tube, not visible, is located within casing 10. The focal spot of the x-ray tube may be on or displaced from the tube casing rotational axis 14. The tube casing has a collimator, represented by the rectangle 15, mounted on it. The collimator establishes the boundaries of a diverging x-ray beam which emanates from the focal spot. A dashed imaginary vertical line 16 is shown extending between the axis 14 of the tube casing and the rotational axis 42 of an x-ray receptor 40 which will be described below. The central ray of the x-ray beam would be parallel to this line if the focal spot is not on axis 14.

X-ray tube casing 10 is angulated about axis 14 with a reversible servo motor 17 within stand 13. The motor has a power output pinion 18 which is meshed with a gear 19. Gear 19 is meshed with a gear segment 20 which is fastened to the x-ray tube casing 10. It will be evident that when motor 17 is energized rotational force will be transmitted through the gear train including gears 18, 19 and 20 to cause tube casing 10 to angulate in one direction or another about axis 14.

The x-ray table in FIG. 1 is shown somewhat schematically and with the patient supporting cradle omitted. The table includes a pair of upstanding side members 25 and 26 which are spaced from the floor 27. A base 28 for supporting the translatable patient cradle, not shown, is schematically represented as being supported on side members 25 and 26. In this embodiment, the x-ray tube casing 10 is adjustable vertically with the components of the table which were just mentioned. Thus, the x-ray tube stand 13 is mounted on a plate 29 which is fastened by means of brackets 30 and 31 to the side members 25 and 26. A motor 32 having a gear box 33 is used for driving plate 29 and, hence, the table structure, in opposite directions vertically. Cross shafts such as the one marked 34 extend from the gear box and are operatively engaged with lead screws such as the one marked 35. The lead screws turn in internally threaded collars 36 which are fastened in plate 29. It will be evident that when motor 32 operates, it will turn lead screws 35 and cause plate 29 and the x-ray tube casing 10 and the whole table to move up or down in accordance with the direction in which the motor 32 is turning. The components of the x-ray table which are illustrated are encased in an x-ray shielding housing, not shown.

The x-ray beam emanating from the focal spot in tube casing 10 is projected upwardly through a patient, who would be located above table top base 28, and toward the x-ray image input end of an image receptor such as the electronic image intensifier which is generally designated by the reference numeral 40. An ordinary x-ray fluorescent screen, not shown, might be substituted for the image intensifier 40 in some kinds of x-ray apparatus. Moreover, the image intensifier could be located within the x-ray table and the x-ray source could be located above the table.

The image intensifier 40 may be considered to be a well-known type which is characterized by having an x-ray image fall on a planar fluorescent screen which is symbolized by the dashed line 41 within the image intensifier housing. As is well-known, in electronic intensifiers of this kind, the fluorescent image on screen 41 is converted to an electron image which, in turn, is focused on a phosphorescent screen, not shown, which converts the electron image to a bright, minified visible image. This visible image is viewed through an optical system including a video camera and displayed on a video monitor, not shown. The optical and video systems have been omitted from the drawing for the sake of simplifying it.

The image receptor, that is, image intensifier 40 in this example, is supported for rotating or angulating about a shaft axis 42. Axis 42 about which image intensifier 40 turns or angulates is parallel with the angulation axis 14 of x-ray tube casing 10. If tube casing axis 14 is offset from the focal spot of the x-ray tube, axis 42 of the intensifier should be similarly offset from the center of screen 41 so the central ray of the x-ray beam always falls on the center of the screen.

Image intensifier 40 is supported for angulation on an arm 43. This arm is fastened at one end 44 to the lower end of a vertically extending column 45 which telescopes and moves vertically within a vertically immovable hollow column 46. Usually the arm support is made up of more than one telescoping column or section such as the one marked 45 so that the image intensifier can be moved through a substantial vertical distance. Column section 46 is mounted to a carriage 47 which has wheels such as the one marked 48 to enable the carriage to run on a stationary track member 49 which is usually mounted near the ceiling of the room in which the x-ray apparatus is located. It will be evident that having the image intensifier 40 mounted on the telescoping support enables it to be adjusted vertically to various heights with respect to the patient supporting table and with respect to the focal spot of the x-ray source. The intensifier 40, as a result of being mounted on carriage 47, can also be translated in opposite directions from its illustrated solid line position longitudinally of the x-ray table top. For convenience, longitudinal movement in either direction is considered the x direction or vector in this direction. Movement of the image intensifier vertically, is considered to be movement in the y direction or along the y vector. When image intensifier 40 is in home position, the angulation axis 42 of the intensifier is truly vertical over the angulation axis 14 of the x-ray source as suggested by the imaginary dashed vertical line 16, but if the focal spot were offset and the center of screen 41 were offset from their axes 14 and 42, line 16 would be parallel to the central ray of the x-ray beam.

In this example, the image intensifier 40 is positioned in the x and y directions manually by the operator applying suitably directed forces to a handle 50 which is fastened to the image intensifier support arm 43.

In FIG. 1, image intensifier or receptor 40 is angulated about axis 42 with a servo motor 51 which is mounted to arm 43. This is a combination motor and gear reduction box from which a power output shaft 52 extends. A wormgear 53 is turned by shaft 52. This wormgear engages with a segmental wormwheel 54 which is fastened to the intensifier and turns it on the shaft which has axis 42 when reversible servo motor 51 is energized.

In FIG. 1 the image intensifier 40 is represented by phantom lines in one of the positions to which it may be translated and angulated. Now for the central ray of the x-ray beam to be perpendicular to the image input plane 41 it is necessary to angulate the x-ray tube casing through an angle $\theta S$ which is the angle between the vertical axes connecting line 16 and the angulated line 16'. The image intensifier 40 must also be angulated as shown, through an angle $\theta I$ which is an angle between line 16' and the imaginary vertical dashed line 55 which is parallel to the vertical line 16. A condition for the central ray of the x-ray beam being perpendicular to and centered on the image input plane 41 is that $\theta I$ must equal $\theta S$. $\theta I$ and $\theta S$ will have a value that depends upon how far the image intensifier angulation axis 42 is translated horizontally or along the x vector from home position and will also depend on the elevation of the image intensifier axis 42 relative to the angulation axis 14 of the x-ray tube. Thus, the vertical line 16 becomes part of a triangle in which the side adjacent the angle $\theta S$ has a length corresponding with the distance from the x-ray tube axis 14 to the image intensifier angulation axis 42. The other line 16' which diverges from the vertical line 16 by the angle $\theta S$ is the resultant vector of the triangle. The side of the triangle opposite of angle $\theta S$, that is, the x vector, has a length corresponding with the distance through which the image intensifier angulation axis 42 is translated horizontally from home position.

An organ such as the heart is shown schematically in a dashed outline and marked 56 in FIG. 1. The left descending artery of this heart may lie in a plane 57 which is illustrated as being disposed at an acute angle with respect to horizontal. By reason of image intensifier 40 now being angulated as depicted in phantom lines, the axes connecting line 16' and the x-ray beam itself will be perpendicular to plane 57 so that the entire length of this artery can be imaged without foreshortening. The user will usually also translate the receptor sufficiently to enable the x-ray beam to pass under other parts of the anatomy which would interfere and prevent a direct view of the organ of interest.

Figure 2:
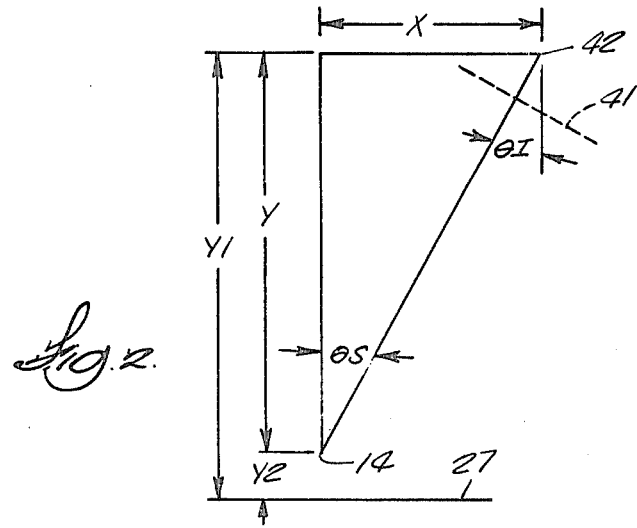
FIG. 2 is a diagram which is useful for explaining operation of the improved x-ray apparatus control system.

FIG. 2 shows a triangle for determining the x and y coordinates of the image intensifier axis 42 after the axis has been translated from home position horizontally or in a combination of horizontal and vertical movements. The net horizontal distance of the image intensifier axis 42 travel from home position is represented by the vector x. The net distance between the height of the axis 42 and the axis 14 is represented by the vector Y. The direction of the axis-to-axis line 16', which is the resultant vector and hypotenuse of the triangle extends from the focal spot FS to the point 42 where the axis of the image intensifier has come to rest. Since the x-ray tube casing 10 and x-ray table can be raised and lowered jointly as explained earlier, the focal spot FS may be at different distances Y2 from a reference plane which could be the floor 27. The height of the intensifier axis 42 from the reference plane 27 is equal to Y1 as indicated in FIG. 2 and the height of this axis relative to the focal spot, that is, the distance Y, results from subtracting Y2 from Y1. The angles $\theta S$ and $\theta I$ indicative, respectively, of the equal angles through which the x-ray source and x-ray image intensifier are turned in response to moving the intensifier are also indicated on FIG. 2.

Some control signals are required for the servo control system which will be discussed later in connection with FIG. 3. In the FIG. 1 apparatus, these control signals are obtained by operating potentiometers in correspondence with the various movements which the image intensifier executes. The signals are related to the x and y vectors and the angles $\theta S$ and $\theta I$ in FIG. 2.

Near the top of FIG. 1, a potentiometer PX is represented. This potentiometer produces a variable output signal which is proportional to the distance that the image intensifier and, hence, carriage 47 depart from home position in the longitudinal or x direction. In other words, the signal from potentiometer PX is proportional to the x vector in FIG. 2.

Another potentiometer is marked PY1. Its output signal is varied by vertical movement or arm 43 which is mounted on the telescoping support including sections 45 and 46. This signal, by itself, is not truly representative of the distance between the x-ray tube angulation axis 14 and image intensifier axis 42 because the focal spot is subject to being raised and lowered under the influence of motor 32 within the x-ray table. Hence, another potentiometer PY2, shown schematically adjacent the x-ray table produces an output signal representative of the height of the axis 14 with respect to a reference plane, or, in other words, the signal is proportional to the distance Y2 in FIG. 2. Subtracting the PY2 signal from the PY1 signal produces a net signal Y which corresponds with the true height of the image intensifier axis 42 relative to the focal spot of the x-ray tube on its axis 14. It will be evident that if a signal corresponding with the x direction and distance is divided by a signal corresponding with the distance y between the two rotational axes, the resulting signal will correspond with the tangent of the angle $\theta S$ and, $\theta I$ also, in FIG. 2.

As indicated at the outset, the new system for inhibiting an x-ray exposure unless the x-ray image intensifier and x-ray source are at the same angle and aligned with each other also uses an independent signal corresponding with the tangent of $\theta S$ and $\theta I$. Referring to FIG. 1, a signal corresponding with the instantaneous value of the tangent of $\theta I$ during angulation, that is, the angle of the image intensifier with respect to a vertical line, is obtained with a linear potentiometer 60 which is mounted on a plate 61 and is supported from arm 43. This potentiometer has a slideable operating rod 62 extending from it. Axial movement of the rod varies the resistance and, hence, the value of the output signal that is obtained from the potentiometer. Rod 62 terminates in a yoke 63 which is pinned at 64 to make a swivel connection with a linear bearing 65. Bearing 65 is slideable on a rod 66 which is driven and caused to swing about an arc whose center is coincident with image intensifier angulation axis 42. Swinging arm 66 is fastened to the same shaft as is a sprocket 67. When the image intensifier is angulated by servo motor 51, arm 66 swings through a corresponding angle $\theta I$. As a result of arm 66 swinging through an arc, linear potentiometer 60 will produce an output signal that is proportional to the tangent of $\theta I$ in radians as has been proved mathematically. In FIG. 3, potentiometer 60 is similarly marked and is called a feedback pot.

Another signal corresponding with the instantaneous actual value of the angle $\theta I$ and not its tangent is also produced when the image intensifier 40 is angulated. This is done by having a sprocket 67 drive a small sprocket 68 with a toothed timing belt 69. Small sprocket 68 turns the shaft of a potentiometer 70 which is shown in dashed lines in FIG. 1 and will be discussed further when the FIG. 3 block diagram is discussed. The output signal from potentiometer 70 is linearly proportional to the angle $\theta I$.

Signals corresponding with the actual instantaneous angle $\theta S$ in radians and the tangent of the angle $\theta S$, respectively, are also produced coincidentally with the x-ray tube casing 10 being angulated by its servo motor 17. $\theta S$ stands for the angle of the x-ray source relative to a vertical line through the x-ray tube casing axis 14. The signal corresponding with the tangent of $\theta S$ is produced with a linear potentiometer 75 which has a slide rod 76 terminating in a yoke 77 that makes a swivel connection with a linear bearing 78. Linear bearing 78 is slideable on a rod 79 which swings through an arc about the axis 14 through an angle corresponding with the angle $\theta S$ through the x-ray tube casing is driven by its servo motor 17.

The other signal, mentioned in the preceding paragraph, corresponding with $\theta S$ rather than tangent of $\theta S$ is produced by driving a potentiometer 80 shown in dashed lines in FIG. 1. Potentiometer 80 produces an output signal that varies in direct correspondence with $\theta S$. This potentiometer is driven with a sprocket 81 which turns with the x-ray tube casing 10 about axis 14 when the casing is driven angularly. Sprocket 81 runs over an idler sprocket 82 and drives potentiometer sprocket 83 by means of a timing belt 84.

Now that the means for producing all of the essential signals for the servo control system and for the new x-ray exposure inhibiting system have been described, these systems will be described in reference to FIG. 3.

In the upper right area of FIG. 3, a relay coil 85 is shown. One of its ends is connected to a +V voltage source and the other of its end is connected to the collector of a transistor 86. When this transistor is turned off, coil 85 becomes deenergized and the x-ray tube output is inhibited. Coil 85 is illustrated as operating a contact 87 which is closed when coil 85 is deenergized. Contact 87 is in a series circuit with an indicator lamp 89 which connects between +V and ground. Deenergization of relay 85 occurs when conditions are not right for making an x-ray exposure in which case contact 87 will be closed to provide a warning by means of indicator lamp 89. The other contact 88 is closed when coil 85 is energized. When open, contact 88 disables the x-ray tube power supply, not shown, so that no x-ray exposure can be taken until all necessary conditions are met. As indicated earlier, x-ray exposures are inhibited whenever the x-ray source and x-ray image intensifier have not reached their final angulation positions and also when there has been a loss of electric power or failure of an electronic, electrical or mechanical component which would prevent the system from driving properly. Loss of power on coil 85, causes fail-safe opening of x-ray control contact 88.

As stated, relay coil 85 is energized when transistor 86 is turned on. This transistor turns off when the output of a gate 90 goes high in which case there is no driving current for the base emitter circuit, including inverter 96 and resistor 91, of transistor 86. One of the inputs to gate 90 is normally held at a low logic level as a result of being connected through a resistor 98 to a DC source marked +V. The ungrounded input to gate 90 connects to a common line 92 through a resistor 93. When line 92 goes to a logic low as is the case when conditions are improper for making an x-ray exposure, the gate 90 output goes high, the inverter 96 output goes low, transistor 86 turns off, and warning lamp contact 87 closes and x-ray power supply control or disabling contact 88 opens.

The servo motor system and the new apparatus for inhibiting an x-ray exposure until conditions required for making a proper x-ray exposure are met will now be described in reference to FIG. 3.

First to be described is the manner in which the main command signal for the x-ray casing angulating servo system, which is one of the signals corresponding with tangent $\theta S$, is developed as a result of translating the image receptor so its rotational axis 42 is at a vertical distance y from the x-ray source axis 14 and at a horizontal distance x from the point where the image receptor angulation axis is vertically over the source axis 14. The signal corresponding with the x distance, as in FIG. 2, is obtained with potentiometer PX and is supplied over a line 95 to a scaler 96 in FIG. 3. A signal corresponding with the y distance, obtained by subtracting Y2 from Y1, is supplied by way of a line 97 to corresponding inputs of a pair of analog dividers 101 and 125.

The signal, corresponding with the scaled x distance or vector are supplied by way of line 99 to the other inputs of analog signals dividers and 125. Dividing the x signal by the y signal results in divider 101 outputting a servo system command signal, corresponding with tangent $\theta$, on its output line 102. This signal is one input to a summing or subtracting device 103. Another signal, corresponding with tangent $\theta$ derived from previously described potentiometer 75, constitutes another input to summing device 103 by way of line 104. Immediately after any translation of image receptor axis 42 to a new position, summing device 103 puts out an error signal on a line 105. This error signal is fed to the servo control system for x-ray source angulation motor 17. The servo system up to this point is conventional in that it has a signal processing or compensation circuit symbolized by the block 106 and a servo amplifier indicated by the block 107. The servo amplifier, in a conventional manner, energizes motor 17 as long as an error signal or motor command signal, exists.

As mentioned earlier, the signal corresponding with tangent $\theta$ resulting from dividing signals corresponding with the x and y vectors is compared with another signal corresponding with tangent of $\theta$ in radians that is obtained by driving linear potentiometer 75 with swinging arm 79 which is at the angle $\theta S$ of x-ray source angulation at any instant. The feedback potentiometer 75, shown as a block in FIG. 3, produces the instantaneous or real time signal corresponding with tangent $\theta$ in radians and provides it to algebraic summing device 103 by way of line 104. Summing device 103 and other summing devices mentioned herein produce an output or error signal which is equal to the difference between their input signals. Hence, the term summing device is used herein in its broadest sense to include signal addition and subtraction. When motor 17 drives the x-ray source to the angle where the signal corresponding with the tangent of $\theta S$ from feedback potentiometer 75 becomes equal to the value of tangent $\theta S$ resulting from dividing the x and y signals, the output from summing device 103 is zero or nulled in which case motor 17 discontinues angulating x-ray source 10 on its axis 14.

While x-ray source motor 17 is driving, the image receptor angulation motor 51 is also angulating the image receptor. This is accomplished by providing the output signal from divider 101 to one input of another summing device 108 by way of line 109. The signal on line 109 is the command signal to the image intensifier servo motor 51 servo system which includes a servo amplifier 110 and a signal processing circuit 111. The command signal on line 109 corresponds, of course, with tangent $\theta S$ so the same command signal is used in the servo systems for source angulation motor 17 and image receptor angulation motor 51. While image receptor 40 is being angulated substantially in phase with angulation of the x-ray source, feedback potentiometer 60 is producing a varying signal corresponding with tangent of $\theta I$ in radians on line 112 which is another input to summing device 108. Again, when the signal corresponding with tangent $\theta I$ on line 112 equals the calculated value of the signal corresponding with the tangent $\theta S$, summing device 108 produces a null or zero signal on its output line 113 and servo motor 51 stops.

In accordance with the invention, making of an x-ray exposure is inhibited at any time that the image receptor angle $\theta I$ does not equal the source angle $\theta S$. Such would be the case while one or the other or both of the image receptor motor 51 and the source motor 17 are still driving. Any misalignment of the source and receptor resulting from failure of a servo system component such as a motor, potentiometer or wiring which would prevent a receptor and source from ever being properly angulated and aligned also results in x-ray exposures being inhibited.

X-ray exposures are inhibited whenever an angular error exists by comparing the command signal errors for the image receptor and x-ray source in window comparators which determine whether the errors are within acceptable limits. If they are not, x-ray is inhibited.

The comparator, shown in block form in FIG. 3, for detecting x-ray source angulation error is marked 115. Comparator 115 has an input line 116 and an output line 117 which connects to a common line 92. The input to comparator 115 is the error signal resulting from the present difference between the value of tangent $\theta$ resulting from dividing the x and y signals and the tangent $\theta S$ signal from feedback potentiometer 75. As long as these two signals, corresponding with the tangent of the angle to which the receptor has been translated and the tangent of the angle through which the x-ray source is presently angulated differ, the output 117 of the comparator will be maintained in a logic 0 or low logic state. When output 117 is low, common line 92 is also held low in which case energization of the x-ray source is prohibited because, as was explained earlier, this turns off transistor 86, deenergizes relay 85 and holds x-ray control contact 88 open and warning lamp contact 87 closed. When the error signal is reduced to within the predetermined limits, the output 117 of comparator 115 goes high, thereby allowing transistor 86 to turn on and allowing closure of x-ray control circuit contact 88 so that, if all other conditions were met, an x-ray exposure could be made.

One of the other conditions that must be met is that the image receptor 40 must also be at the same angle as the x-ray source and a signal corresponding with the instantaneous value of tangent $\theta I$ produced by feedback potentiometer 60 during image receptor angulation must have reached equality with the value of tangent $\theta$ resulting from division. In other words the error signal on the output 113 of summing device 108 must be reduced to within the specified limits. Thus, another window comparator 118 is provided for sensing the magnitude of the error in the servo loop for image receptor angulation motor 51. Comparator 118 is functionally similar to comparator 115 which has been described. As long as there is a significant error signal on line 113, the output line 119 of comparator 118 remains low so as to hold common line 92 in a logic low x-ray inhibiting state. This prevents x-ray power supply control contact 88 from closing. When the error signal fed to comparator 118 is within specified limits, output 119 of comparator 118 goes to a logic high so that common line 92 can go high to thereby enable x-ray control relay contact 88 to close if line 92 is not otherwise held low because of some other required condition for exposure not having been met.

Because it is so important to inhibit an x-ray exposure if the x-ray source and image receptor are not coordinately angulated and aligned, another system is provided for determining if the source and receptor are properly oriented and not in motion. This backup or redundant system depends on comparing signals corresponding with the actual measured values of $\theta S$ and $\theta I$ with the error or command signal that is supplied to the two servo systems. Thus, in FIG. 3, a signal corresponding with $\theta I$ is inputted on line 121 to a scaling and signal level changing device 122. The signal corresponding with $\theta I$, that is, the actual angle of the image receptor is, as was explained earlier, obtained by driving a potentiometer 70 whose output is linearly related to the instantaneous actual angle through which image receptor 40 is angulated about its axis 42. This signal is outputted on line 123 which is one input to a summing device 124. The other input to summing device 124 is the output from another divider 125 which, like divider 101, outputs a signal on line 126 corresponding with tangent $\theta S$ resulting from division of signals corresponding with the x and y positions of the image receptor axis 42. For small angles, a signal corresponding with the angle $\theta I$ is substantially equal to a signal corresponding with tangent of $\theta I$. Thus, these signals provide a good basis for comparison in the small angular error range. The signals are summed or subtracted in summing device 124. If there is a difference between them, an error signal appears on output line 127 of summing device 124. A window comparator 128 determines if the error signal and, hence, the image receptor angular error, is within limits. If it is not within limits, that is, if $\theta I$ is not yet nearly equal to the value it should have for the location of the x and y coordinates of the image receptor axis 42, the output line 129 from comparator 128 will be at a logic low level, to thereby hold common line 92 low and inhibit making an x-ray exposure by virtue of control contact 88 being held open.

Another circuit is provided for independently determining if θS, the present angle of the x-ray source, has reached the angle it should be at for whatever x and y coordinates the image receptor has been translated to. The additional circuit is comparable to the one just described. It comprises a scaling device 131 having an input 132 that is supplied with a signal corresponding with the angle θS. This is the signal produced by potentiometer 80 in FIG. 1 and is linearly related to the present angle through which x-ray source 10 has angulated about its axis 14. This circuit includes a summing device 133 having an input 134 for receiving the signal corresponding with the angle θS. It has another input 135 for receiving the redundant command signal from the output of divider 125 by way of lines 126 and 135. As long as there is a difference between the signal corresponding with θS and the signal corresponding with tangent θS resulting from division of the x and y position values, there will be an error signal on the output line 136 of summing device 133. The error signal is fed to a window comparator 137 which is similar to comparator 128 in that its output line 138 goes low if there is significant angular error and goes high when the error is within limits. Output line 138 is coupled to common line 92 so it will pull the common line low and inhibit energization of the x-ray source if the measured value of θS is not very close to the calculated value of the angle obtained by division.

Any of the signals corresponding with angle may be used to drive a digital display, not shown, for displaying to the operator the angle at which the image receptor is angulated at any time.

A typical scaling circuit such as the one in block 122 is depicted in FIG. 4. Its input is marked 121 as it is in FIG. 3. The scaling circuit comprises an operational amplifier 141 having a feedback resistor 142, an input resistor 143 and an input circuit potentiometer 144. The wiper of potentiometer 144 is in circuit with resistors 145 and 146 which act as a divider. Potentiometer 144 is adjusted to establish the proper scale factor for the scaling device. Another potentiometer 147 is for balancing or adjusting the output to zero when the angle θI equals 0, that is, when the image intensifier is vertically oriented. The output of the scaling device which is used for illustration is marked 123 in FIG. 4 as it is in FIG. 3.

An illustrative comparator comparable to any of those marked 111, 118, 128 and 137 is shown in FIG. 5. Assume it is the one marked 128 in FIG. 3. Its input is marked 127 and its output is marked 129 in FIG. 5 as it is in FIG. 3. The window comparator comprises two voltage comparators 149 and 150. When the output of either comparator goes low, common line 92 is pulled low. The input or error signal is supplied from line 127 through an input resistor 151 that connects alternately to the inverting and noninverting inputs of the comparators 149 and 150. Comparator 149 has its noninverting input supplied with a reference signal obtained through an input resistor 152 from a divider comprised of resistor 153 and a potentiometer 154.

The noninverting input of comparator 150 is supplied with a reference voltage signal through an input resistor 155 and which signal is derived from a divider comprised of resistor 156 and potentiometer 157. In accordance with a well-known property of window comparators, if the error signal supplied on line 127 is below the upper limit reference voltage signal from potentiometer 154 and above the reference voltage signal from potentiometer 157, in this example, the outputs 129 of the comparators will be at a logic high level so that x-ray source energization may be enabled at that time. If the error signal on line 127 is above the reference signal from potentiometer 154 or below the signal from potentiometer 157, output 129 will switch to a logic low and, in this example, energization of the x-ray source would be inhibited.

Although the invention has been described in detail, such description is intended to be illustrative rather than limiting, for the invention may be variously embodied and is to be limited only by interpretation of the claims which follow.

I claim:

1. In x-ray apparatus including an x-ray source device for projecting an x-ray beam from its focal spot, an x-ray receptor device spaced from said source to enable an examination subject to be disposed in the beam from the source to the receptor, means for mounting said source device and said receptor device, respectively, for angulation about their respective first and second axis, the angulation axis of one of said source device and said receptor device being stationary and the other of said source and said receptor devices and its angulation axis being translatable along a first line having a length designated as the x distance and constituting one side of a triangle, said first line being perpendicular to a second line extending between said axes and having a length designated as the y distance and constituting another side of said triangle, a line extending between the axis of the untranslated device and the axis of the translated device constituting the hypotenuse of said triangle and defining with said second line an angle designated as θ, and first and second servo systems including motor means operative to angulate said source and said receptor, respectively, each of said servo systems including control means having input means for an error signal and having output means supplying driving power to the servo motors for angulating said devices in response to error signals, respective means for developing first signals each corresponding with the varying instantaneous values of the tangents of the angles (in radians) in which said devices are angulated during operation of said motor means and during concurrent angulation of said image receptor and said x-ray source means while an error signal exists, means for developing x distance and y distance related signals proportional, respectively, to the said x and y distances which define the position to which one device has been translated, means for dividing said signal proportional to the x distance by the signal proportional to the y distance to produce a servo system command signal proportional to the tangent of θ, means for producing respective angulation error signals for said receptor and said source representing the differences between said command signal corresponding with tangent of θ resulting from division and each of said instantaneous varying signals corresponding with the tangents of the angulation angles in radians, said servo motors operating until being interrupted in response to nulling of said error signals, individual means either of which is responsive to the existence of one error signal by preventing energization of said x-ray source, means for producing a signal corresponding directly with the value of the angle to which said x-ray source has been angulated at any instant during angulation following translation of said one of said image receptor and x-ray source, means for producing an error signal representative of the difference between said signal corresponding with said instantaneous angulation and the command signal corresponding with the tangent of $\theta$, means responsive to the existence of said last named error signal by preventing energization of said x-ray source, means for producing a signal corresponding directly with the value of the angle to which said receptor has been angulated at any instant following translation of one of said image receptor and said source, means for producing an error signal representative of the difference between said last named signal and the command signal corresponding with the tangent of $\theta$, and means responsive to existence of said last named error signal by preventing energization of said x-ray source.

2. The apparatus as in claim 1 wherein said means for producing a signal corresponding with the tangent of the instantaneous angle of said translated device comprises:

linear potentiometer means, a radially extending arm coupled for swinging through the same angle through which said untranslated device is being angulated by said servo motor means, a bearing element mounted for sliding radially on said arm and a swivel element coupled for swiveling on said bearing element, said linear potentiometer means including a shaft that is movable linearly to vary the resistance of said potentiometer, said shaft having one end coupled to said swivel element for being moved as said arm swings, whereby as said arm swings, through an angle, said potentiometer will develop said signal corresponding with the tangent of said angle in radians.

3. The apparatus as in claim 1 wherein said means for producing a signal corresponding with the tangent of the instantaneous angle of said untranslated device comprises:

linear potentiometer means, a radially extending arm coupled for swinging through the same angle through which said image receptor is being angulated by said servo motor means, a bearing element mounted for sliding radially on said arm and a swivel element coupled for swiveling on said bearing element, said linear potentiometer means including a shaft that is movable linearly to vary the resistance of said potentiometer, said shaft having one end coupled to said swivel element for being moved as said arm swings whereby as said arm swings through an angle said potentiometer will develop said signal corresponding with the tangent of said angle in radians.

4. In x-ray apparatus including an x-ray source for projecting an x-ray beam from its focal spot, an x-ray receptor spaced from said source to allow an examination subject to be disposed in the path of the beam from said source, servo motor systems each including control means and motor means for angulating said source and said receptor, respectively, through opposite angles until they are aligned and at the same angle with respect to a reference line, first means for producing a signal corresponding with the tangent of the angle subtended by a vector coextensive with the distance through which said receptor has been translated away from said reference line, a plurality of second means for producing signals corresponding with the instantaneous value of the tangents of the angles through which said receptor and said source are angulated when angulation is in progress under the influence of the respective servo motor means, said second means each comprising a radially extending arm for swinging through the same angle as said source and receptor are angulated, a bearing element slideable on said arm, a linear potentiometer operative to produce said second signals which correspond with the instantaneous value of the tangents of the angulation angles, an operating shaft extending from said potentiometer and means connecting said shaft pivotally to said slideable bearing element, swinging of said arm thereby resulting in the amount of shaft movement which corresponds to the tangent of the angle through which said arm swings, means for comparing the signals corresponding with the instantaneous values of the tangents with said first signal, respectively to produce error signals representative of the difference between said compared signals, said servo systems responding to said error signals by causing said servo motors to angulate said source and receptor until said error signals are null.

* * * * *